US007960424B2

(12) United States Patent
Calderari et al.

(10) Patent No.: US 7,960,424 B2
(45) Date of Patent: *Jun. 14, 2011

(54) LIQUID PHARMACEUTICAL FORMULATIONS OF PALONOSETRON

(75) Inventors: Giorgio Calderari, Rancate (CH); Daniele Bonadeo, Varese (IT); Roberta Cannella, Varese (IT); Enrico Braglia, Pazzallo (CH); Riccardo Braglia, Pazzallo (CH); Andrew Miksztal, Palo Alto, CA (US); Thomas Malefyt, Carmel Valley, CA (US); Kathleen M. Lee, Palo Alto, CA (US)

(73) Assignees: Helsinn Healthcare S.A., Lugano (CH); Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/388,270

(22) Filed: Mar. 24, 2006

(65) Prior Publication Data

US 2006/0167073 A1  Jul. 27, 2006

Related U.S. Application Data

(63) Continuation of application No. 11/186,311, filed on Jul. 21, 2005, now Pat. No. 7,947,724, which is a continuation of application No. PCT/EP2004/000888, filed on Jan. 30, 2004.

(60) Provisional application No. 60/444,351, filed on Jan. 30, 2003.

(51) Int. Cl.
*A01N 43/52* (2006.01)
(52) U.S. Cl. ...................................... 514/397
(58) Field of Classification Search ................. 514/397
See application file for complete search history.

(56) References Cited

U.S. PATENT DOCUMENTS

| 4,695,578 | A | 9/1987 | Coates et al. ............... 514/397 |
| 4,753,789 | A | 6/1988 | Tyers et al. ................. 424/10 |
| 4,886,808 | A | 12/1989 | King ......................... 514/299 |
| 4,906,755 | A | 3/1990 | Gittos ....................... 546/94 |
| 4,929,632 | A | 5/1990 | Tyers et al. ................. 514/397 |
| 4,937,247 | A | 6/1990 | King ......................... 514/299 |
| 5,011,846 | A | 4/1991 | Gittos et al. ................ 514/294 |
| 5,034,398 | A | 7/1991 | King ......................... 514/299 |
| 5,202,333 | A | 4/1993 | Berger et al. ............... 514/299 |
| 5,240,954 | A | 8/1993 | Tyers et al. ................. 514/395 |
| 5,272,137 | A | 12/1993 | Blase et al. |
| 5,344,658 | A | 9/1994 | Collin ....................... 424/489 |
| 5,578,628 | A | 11/1996 | Tyers et al. ................. 514/397 |
| 5,578,632 | A | 11/1996 | Tyers et al. ................. 514/397 |
| 5,622,720 | A | 4/1997 | Collin ....................... 424/489 |
| 5,854,270 | A | 12/1998 | Gambhir |
| 5,922,749 | A | 7/1999 | Tyers et al. ................. 514/397 |
| 5,955,488 | A | 9/1999 | Winterborn ................ 514/399 |
| 6,063,802 | A | 5/2000 | Winterborn ................ 514/397 |
| 6,284,749 | B1 * | 9/2001 | Castillo et al. .............. 514/159 |
| 6,287,592 | B1 | 9/2001 | Dickinson |
| 6,294,548 | B1 | 9/2001 | James ........................ 514/299 |
| 2001/0020029 | A1 | 9/2001 | James ........................ 514/299 |
| 2003/0095926 | A1 | 5/2003 | Dugger, III ................. 424/43 |

FOREIGN PATENT DOCUMENTS

| WO | WO 03/100091 A | 12/2003 |
| WO | WO-2004045615 A1 * | 6/2004 |
| WO | W02004067005 | 8/2004 |
| WO | WO-2004073714 A1 * | 9/2004 |

OTHER PUBLICATIONS

Matsumoto et al., "Yakuzaigaku Manual", 1st edition, Nanzando Co., Ltd. (1989) 2 pages.*

Barton (Citrate Buffer Calculation, 2000, 2pgs.*

Eglen, R. M. et al., Pharmacological Characterization of RS 25259-197, a Novel and Selective 5-$HT_3$ Receptor Antagonist, in vivo, extracted from *British Journal of Pharmacology*, 1995, vol. 114, No. 4, pp. 860-866.

Chelly, Jacques et al., Oral RS-25259 Prevents Postoperative Nausea and Vomiting Following Laparoscopic Surgery, extracted from *Anesthesiology*, 1996, vol. 85, No. 3A, p. A21.

Sorbe, Bengt, 5-$HT_3$ Receptor Antagonists as Antiemetic Agents in Cancer Chemotherapy, extracted from *Expert Opinion on Investigational Drugs*, 1996, vol. 5, No. 4, pp. 389-407.

Gaster, Laramie M. and King, Frank D., Serotonin 5-$HT_3$ and 5-$HT_4$ Receptor Antagonists, extracted from *Medicinal Research Reviews*, 1997, vol. 17, No. 2, pp. 163-214.

Tang, Jun et al., Efficacy of RS-25259, a Novel 5-$HT_3$ Antagonist, in the Prevention of Postoperative Nausea and Vomiting After Major Gynecologic Surgery, abstract extracted from *Anesthesiology*, 1997, vol. 85, No. 3, suppl. p. A329.

Tang, Jun et al., The Efficacy of RS-25259, a Long-Acting Selective 5-$HT_3$ Receptor Antagonist, for Preventing Postoperative Nausea and Vomiting After Hysterectomy Procedures, extracted from *Anesthesia and Analgesia*, 1998, vol. 87, pp. 462-467.

Adis R&D Profile, Palonosetron RS 25259, RS 25259 197, extracted from *Drugs in R&D*, Oct. 1999, vol. 2, No. 4, pp. 251-252.

Piraccini, Gaia et al., An Interesting 5-$HT_3$ Receptor Antagonist Antiemetic for Patients Undergoing Chemotherapy-Based Conditioning Regimens?, extracted from *Blood*, Nov. 16, 2001, vol. 98, No. 11, part 2, p. 350b, abstract No. 5169.

Stacher, Georg, Palonosetron Helsinn, extracted from *Current Opinion in Investigational Drugs*, Oct. 2002, vol. 3, No. 10, pp. 1502-1507.

(Continued)

*Primary Examiner* — Michael G Hartley
*Assistant Examiner* — Shirley V Gembeh
(74) *Attorney, Agent, or Firm* — Arnall Golden Gregory LLP; Clark G. Sullivan

(57) ABSTRACT

The present invention relates to shelf-stable liquid formulations of palonosetron for reducing chemotherapy and radiotherapy induced emesis with palonosetron. The formulations are particularly useful in the preparation of intravenous and oral liquid medicaments.

6 Claims, No Drawings

OTHER PUBLICATIONS

Navari, Rudolph M., Pathogenesis-Based Treatment of Chemotherapy-Induced Nausea and Vomiting—Two New Agents, extracted from *Journal of Supportive Oncology*, 2003, vol. 1(2), pp. 89-103.

Michael J. Pikal, "Freeze Drying", Encyclopedia of Pharmaceutical Technology, Third Edition, Jan. 2007, pp. 1824-1825, vol. 3, Informa Pharmaceuticals & Healthcare.

Oppostion Brief filed by Dr. Reddy's Laboratories (UK) Limited, opposition to European Patent No. 1601359 B1, Jul. 7, 2009.

Photolytic and oxidative degradation of an antiemetic agent, RG 12915 (Won C. M. Et al, International Journal of Pharmaceutics 121 (1995) 95-105 (1995).

Palonosetron: a phase II dose ranging study to assess over a 7 day period the single dose pharmacokinetic profile of palonosetron in patients receiving highly emetogenic chemotherapy. Piraccini G et al., Proc. Am. Soc. Clin. Oncol 2002 21 Abs 449 (2002).

Formulation and administration techniques to minimize injection pain and tissue damage associated with parenteral products. Larry A. Gatlin; Carol A Brister Gatlin, [from Injectable Drug Development: Techniques to Reduce Pain and Irritation [Edited by Pramod K. Gupta, Gayle A. Brazeau; Published by Informa Health Care (original copyright of 1999 by Interpharma Press), 1999; ISBN 1574910957, 9781574910957)], p. 401-421.

Parenteral Dosage Forms. Joanne Broadhead. [from Part 11—Early drug development, Pharmaceutical preformulation and formulation: a practice guide from candidate drug selection to commercial dosage form [Edited by Mark Gibson; Published by Interpharma Press, 2001; ISBN 1574911201, 9781574911206)], p. 331-353.

Opposition Brief filed by Tecnimede Sociedade Tecnico-Medicinal S.A., opposition to European Patent No. 1601359 B1, Jul. 8, 2009.

Response brief filed by Helsinn Healthcare S.A. dated Jul. 13, 2007, in response to the communication pursuant to Art. 96(2) EPC of Jan. 3, 2007 regarding Serial No. 04 706 657.6-2123.

European Patent Office official communication dated Jul. 19, 2006 regarding Serial No. 04 706 657.6.

Response of Helsinn Healthcare S.A. dated Nov. 29, 2006 regarding EPO official communication dated Jul. 19, 2006.

Lachman et al., The Theory and Practice of Industrial Pharmacy, 1986, third edition, pp. 652-784.

Summary of Product Characteristics for Aloxi 250.

Declaration of Valentino J. Stella, Ph.D.

Opposition Brief filed by Martin Paul White, opposition to European Patent No. 1601359 B1, Jul. 8, 2009.

Wong et al. (1995), in British Journal of Pharmacology, vol. 114, pp. 851-859 and Eglen et al. (1995), in British Journal of Pharmacology, vol. 114, pp. 860-866.

Cover page and pp. 642-644 and 783-784 of The Theory and Practice of Industrial Pharmacy, Third Edition, Lea and Febiger (1986).

Cover page and pp. 514-515 of Modern Pharmaceutics, Second Edition, Marcel Dekker (1990).

Cover page and pp. 142-143 of Pharmaceutical Dosage Forms: Parenteral Medications vol. 1, Second Edition, Marcel Dekker (1992).

Scientific Discussion from the European Public Assessment Report for Aloxi (Palonosetron Hydrochloride).

Kranke et al. 2007, "Recent advances, trends and economic considerations in . . . " Expert Opinion Pharmacother., 8 (18): 3217-3235).

Morrow et al. 1995, Progress in reducing nausea and emesis. Comparisons of ondansetron, granisetron, and tropisetron. Cancer, vol. 76 No. 3 pp. 343-357.

Daniele Bonadeo, "Supplemental Declaration of Daniele Bonadeo 37 C.F.R. 1.132", U.S. Appl. No. 11/388,270, Jun. 8, 2009.

Chaitow, 1990, 3 pages.

USPTO Office Action, U.S. Appl. No. 11/388,268, Filing Date Mar. 24, 2006, Mail Date Mar. 29, 2010.

USPTO Office Action, U.S. Appl. No. 11/129,839, Mail Date Jan. 15, 2010.

Israili, Zafar H., Clinical Pharmacology of Serotonin Receptor Type-3 (5-HT3) Antagonists, Curr. Med. Chem.—Central Nervous System Agents, 2001, 1, 171-199.

USPTO Office Action, U.S. Appl. No. 11/201,035, Mail Date Aug. 19, 2009.

Response of Helsinn Healthcare to opposition of EP Serial No. 04 706 657.6 dated Feb. 11, 2010.

Annex 1 (Statement of Waldo Mossi, Ph.D.) to Response of Helsinn Healthcare to opposition of EP Serial No. 04 706 657.6 dated Feb. 11, 2010.

Annex 2 to Response of Helsinn Healthcare to opposition of EP Serial No. 04 706 657.6 dated Feb. 11, 2010.

Annex 3 to Response of Helsinn Healthcare to opposition of EP Serial No. 04 706 657.6 dated Feb. 11, 2010.

$6^{th}$ Edition, Handbook of Pharmaceutical Excipients (2009), pp. 247-250n (RPS Publishing).

* cited by examiner

LIQUID PHARMACEUTICAL FORMULATIONS OF PALONOSETRON

The present invention claims priority to PCT/EP04/000888, filed Jan. 30, 2004, which claims priority to U.S. Provisional Patent Application No. 60/444,351, filed Jan. 30, 2003. The present application is also a continuation of currently pending U.S. patent application Ser. No. 11/186,311, filed Jul. 21, 2005. The content of these applications is incorporated herein by reference.

BACKGROUND OF THE INVENTION

The present invention relates to shelf-life stable liquid formulations of palonosetron that are especially useful in the preparation of injectable and oral medicaments.

Emesis is a devastating consequence of cytotoxic therapy, radiotherapy, and post-operative environments that drastically affects the quality of life of people undergoing such treatments. In recent years a class of drugs referred to as $5-HT_3$ (5-hydroxytryptamine) receptor antagonists has been developed that treat such emesis by antagonizing cerebral functions associated with the $5-HT_3$ receptor. See *Drugs Acting on 5-Hydroxytryptamine Receptors*: The Lancet Sep. 23, 1989 and references cited therein. Drugs within this class include ondansetron, granisetron, alosetron, tropisetron, and dolasetron. These $5-HT_3$ antagonists are often administered intravenously shortly before chemotherapy or radiotherapy is initiated, and can be administered more than once during a cycle of chemotherapy or radiotherapy. In addition, they are often supplied as tablets or oral elixirs to either supplement an intravenous administration, or to ease home usage of the drug if the patient is self-administering the chemotherapeutic regimen.

Because some chemotherapeutic agents can induce emesis over extended periods of several days even when they are administered only once, it would be desirable to administer an emesis-inhibiting drug such as a $5-HT_3$ antagonist every day until the risk of emesis has substantially subsided. The present class of $5-HT_3$ antagonists has not proven especially helpful meeting this need, however, because the $5-HT_3$ receptor antagonists currently marketed have proven to be less effective in controlling delayed nausea and vomiting than they are at controlling acute emesis. Sabra, K, *Choice of a $5HT_3$ Receptor Antagonist for the Hospital Formulary*. EHP, October 1996; 2 (suppl 1):S19-24.

Recently, clinical investigations have been made concerning palonosetron, a new $5-HT_3$ receptor antagonist reported in U.S. Pat. No. 5,202,333. These investigations have shown that the drug is an order of magnitude more potent than most existing $5-HT_3$ receptor antagonists, has a surprising half-life of about 40 hours, and is effective to reduce delayed-onset nausea induced by chemotherapeutic agents. However, formulating palonosetron in liquid formulations has not proven an easy task, typically due to shelf-stability issues. U.S. Pat. No. 5,202,333 discloses an intravenous formulation of palonosetron in example 13 that contains the following ingredients:

| Ingredient | Mg |
| --- | --- |
| Palonosetron HCl | 10-100 mg. |
| Dextrose Monohydrate | q.s. to make Isotonic |
| Citric Acid Monohydrate | 1.05 mg. |

| Ingredient | Mg |
| --- | --- |
| Sodium Hydroxide | 0.18 mg. |
| WFJ | To 1.0 ml. |

The formulation has a pH of 3.7 and a shelf stability of less than the 1-2 year time period required by health authorities in various countries.

Ondansetron, its uses, and medicaments made with ondansetron are disclosed in U.S. Pat. Nos. 4,695,578, 4,753,789, 4,929,632, 5,240,954, 5,344,658, 5,578,628, 5,578,632, 5,922,749, 5,622,720, 5,955,488, and 6,063,802. Commercially it is distributed by GlaxoSmithKline as Zofran® and is indicated for prevention of postoperative nausea and vomiting (PONV), cancer chemotherapy-induced nausea and vomiting (CINV), and radiotherapy-induced nausea and vomiting (RINV) and it is available as an injection, tablets and solution, and as Zofran ODT® (ondansetron) Orally Disintegrating Tablets.

Granisetron, its uses, and medicaments made with granisetron are disclosed in U.S. Pat. Nos. 4,886,808, 4,937,247, 5,034,398 and 6,294,548. Commercially it is distributed by Roche Laboratories Inc. as Kytril®, indicated for the prevention of nausea and vomiting associated with chemotherapy or radiation therapy, and is offered in tablet form, oral solution, and as an injection.

Alosetron, its uses, and medicaments made with alosetron are disclosed in U.S. Pat. Nos. 5,360,800 and 6,284,770. Commercially it is distributed by GlaxoSmithKline as Lotronex®.

Tropisetron is commercially available as Navoban® (Novartis) CAS-89565-68-4 (tropisetron); CAS-105826-92-4 (tropisetron hydrochloride) and it is indicated for treatment of PONV and CINV.

Dolasetron, its uses, and medicaments made with ondansetron are disclosed in U.S. Pat. Nos. 5,011,846, and 4,906,755. Commercially it is distributed by Aventis Pharmaceuticals Inc. as Anzemet®, indicated for prevention of both PONV and CINV, and it is offered in the form of a tablet or an intravenous solution.

Therefore, there exists a need for a palonosetron formulation with increased stability and thereby increased shelf life. There also exists a need for an appropriate range of concentrations for both the $5-HT_3$ receptor antagonist and its pharmaceutically acceptable carriers that would facilitate making a formulation with this increased stability.

It is an object of the present invention to provide a formulation of Palonosetron hydrochloride with increased pharmaceutical stability for preventing and/or reducing emesis.

It is another object of the invention to provide an acceptable range of concentrations which will stabilize a formulation containing Palonosetron hydrochloride.

It is a further object of the invention to provide a formulation of Palonosetron which would allow for prolonged storage.

It is also an object of the invention to provide a formulation of Palonosetron which would allow terminal sterilization.

SUMMARY OF THE INVENTION

The inventors have made a series of discoveries that support a surprisingly effective and versatile formulation for the treatment and prevention of emesis using palonosetron. These formulations are shelf stable for periods eater than 24 months at room temperature and thus can be stored without refrigeration, and manufactured using non-aseptic, terminal sterilization processes.

In one aspect, the inventors have discovered that formulations which include the active ingredient palonosetron require in some instances only $1/10^{th}$ the amount of other previously known compounds for treating emesis, which surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof and b) a pharmaceutically acceptable carrier.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. In another embodiment the invention provides a pharmaceutically stable solution for preventing or reducing emesis comprising from about 0.01 to about 5.0 mg/l palonosetron or a pharmaceutically acceptable salt thereof; from about 10 to about 100 millimoles citrate buffer, and from about 0.005 to about 1.0 mg/ml EDTA.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol.

DETAILED DESCRIPTION OF THE INVENTION

Definitions

"Vial" means a small glass container sealed with the most suitable stopper and seal, other suitable primary containers may be used, for instance but not limited to, p-filled syringes. Vial also means a sealed container of medication that is used one time only, and includes breakable and non-breakable vials, breakable plastic vials, miniature screw-top jars, and any other type of container of a size capable of holding only one unit dose of palonosetron (typically about 5 mls.).

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps "Palonosetron" means (3aS-2,3,3a,4,5,6-Hexahydro-2-[(S)-1-Azabicyclo[2.2.2]oct-3-yl]2,3,3a,4,5,6-hexahydro-1-oxo-1Hbenz[de]isoquinoline, and is preferably present as the monohydrochloride. Palonosetron monohydrochloride can be represented by the following chemical suture:

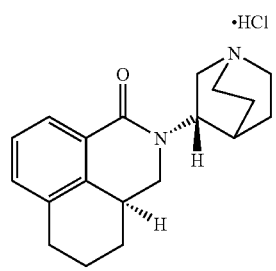

Concentrations—When concentrations of palonosetron are given herein, the concentration is measured in terms of the weight of the free base. Concentrations of all other ingredients are given based on the weight of ingredient added to the solution.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the lie; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Discussion

The fact that palonosetron can be formulated in some instances at concentrations of only about $1/10^{th}$ the amount of other previously known compounds for treating emesis, surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof; and b) a pharmaceutically acceptable carrier. Similarly, in another embodiment the invention provides a method of formulating a pharmaceutically stable solution of palonosetron comprising admixing from about 0.01 mg/mL to about 5 mg/mL palonosetron or a pharmaceutically acceptable salt thereof with a pharmaceutically acceptable carrier. In alternative embodiments, the formulation includes palonosetron or a pharmaceutically acceptable salt thereof in a concentration from about 0.02 mg/mL to about 1.0 mg/mL, from about 0.03 mg/mL to about 0.2 m/mL, and most optimally about 0.05 mg/ml.

A particular advantage associated with the lower dosages of intravenous palonosetron is the ability to administer the drug in a single intravenous bolus over a short, discrete time period. This time period generally extends from about 10 to about 60 seconds, or about 10 to about 40 seconds, and most preferably is about 10 to 30 seconds. In one particular embodiment the palonosetron is supplied in vials that comprise 5 ml. of solution, which equates to about 0.25 mg of palonosetron at a concentration of about 0.05 mg/ml.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. Similarly, in another embodiment the invention provides a method of formulating a pharmaceutically stable solution of palonosetron comprising admixing a) palonosetron or a pharmaceutically acceptable salt thereof; and b) a pharmaceutically acceptable carrier, at a pH from about 4.0 to about 6.0. In alternative embodiments, the pH is from about 4.5 to about 5.5, and most optimally about 5.0. There are many examples to those of skill in the art of suitable solutions to adjust the pH of a formulation. Two exemplary solutions are sodium hydroxide and hydrochloric acid solution, either of which could be used to adjust the pH of the formulation.

In another embodiment the invention provides a pharmaceutically stable solution for preventing or reducing emesis comprising from about 0.01 to about 5.0 mg/ml palonosetron or a pharmaceutically acceptable salt thereof and (i) from about 10 to about 100 millimoles citrate buffer, and/or (ii) from about 0.005 to about 1.0 mg/ml EDTA. Similarly, in another embodiment the invention provides a method of formulating a pharmaceutically stable solution of palonosetron comprising admixing from about 0.01 to about 5.0 mg/ml palonosetron or a pharmaceutically acceptable salt thereof and (I) from about 10 to about 100 millimoles citrate buffer, and/or (ii) from about 0.005 to about 1.0 mg/ml EDTA. The citrate buffer can be in the form of citric acid and/or a salt of citric acid such as trisodium citrate. In various embodiments, the ranges of one or more of the foregoing ingredients can be modified as follows:

The formulation may comprise palonosetron or a pharmaceutically acceptable salt thereof in a concentration from about 0.02 mg/mL to about 1.0 mg/mL, from about 0.03 mg/mL to about 0.2 mg/mL palonosetron hydrochloride; and most optimally about 0.05 mg/ml.

The formulation may comprise citrate buffer in a concentration of from about 10 to about 40 millimoles, or 15-30 millimoles.

The formulation may comprise EDTA in a concentration of from about 0.005 mg/ml to about 1.0 mg/ml, or about 0.3 to about 0.7 mg/ml, and most optimally about 0.5 mg/ml.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol. Similarly, in another embodiment the invention provides a method of formulating a pharmaceutically stable solution of palonosetron comprising admixing a) palonosetron or a pharmaceutically acceptable salt thereof and b) a pharmaceutically acceptable carrier, wherein the pharmaceutically acceptable carrier comprising a chelating agent and mannitol. The chelating agent is preferably EDTA, and, in various embodiments the chelating agent is present in a concentration of from about 0.005 to about 1.0 mg/mL or from about 0.05 mg/mL to about 1.0 mg/mL or from about 0.3 to about 0.7 mg/ml, or most optimally about 0.5 mg/ml. In various embodiments the mannitol is present in a concentration of from about 10.0 mg/ml to about 80.0 mg/ml, from about 20.0 mg/mL to about 60.0 mg/ml, or from about 40.0 to about 45.0 mg/ml.

Injectable formulations are typically formulated as aqueous solutions in which water is the primary excipient. Oral formulations will differ from injectable formulations generally by the additional presence of flavoring agents, coloring agents, or viscosity agents. Natural or synthetic sweeteners include, among others, mannitol, sorbitol, saccharose, saccharine, aspartame, acelsulphame K, or cyclamate. These agents are generally present in concentrations in excess of 100 mg/ml or 250 mg/ml when used as sweetening agents, in contrast to the 41.5 mg/ml concentration of mannitol described in some of the embodiments of the invention, in which mannitol is acting simply as a tonicifying agent.

The formulations of the present invention are particularly suited for use in injectable and oral liquid formulations, but it will be understood that the solutions may have alternative uses. For example, they may be used as intermediates in the preparation of other pharmaceutical dosage forms. Similarly, they may have other routes of administration including intranasal or inhalation. Injectable formulations may take any route including intramuscular, intravenous or subcutaneous.

Still further embodiments relate to improvements in the ease with which the palonosetron formulation can be stored or manufactured. In particular, the inventors have discovered that the formulations of the present invention allow storage of the product for extended periods at room temperature. Thus, in yet another embodiment the invention provides a method of storing one or more containers in which are contained a solution of palonosetron or a pharmaceutically acceptable salt thereof comprising: a) providing a room comprising said one or more containers; b) adjusting or maintaining the temperature of the room at greater than about ten, 15, or 20 degrees celcius; and c) storing said containers in said room for one month, 3 months, 6 months, one year, 18 months, 24 months or more (but preferably not exceeding 36 months), wherein (i) the palonosetron or pharmaceutical salt thereof is present in a concentration of from about 0.01 mg/mL to about 5.0 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent, or (v) the solution comprises from about 10 to about 100 milliMoles of a citrate buffer.

The stability of the foregoing formulations also lends itself well to terminal sterilization processes in the manufacturing process. Therefore, in still another embodiment the invention provides a method of filling a container in which is contained a solution of palonosetron or a pharmaceutically acceptable salt thereof comprising: a) providing one or more sterile open containers (preferably 5 ml. vials); b) filling said containers with a solution of palonosetron in a non-aseptic environment; c) sealing said filled containers; and d) sterilizing said sealed, filled containers, wherein (i) the palonosetron or pharmaceutical salt thereof is present in a concentration of from about 0.01 mg/mL to about 5 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent or (v) the solution comprises from about 10 to about 100 milliMoles of a citrate buffer.

EXAMPLES

Example 1

Stabilizing pH

A study was conducted to determine the effect of pH on formulations containing palonosetron hydrochloride, measuring the stability at 80° C. at pH 2.0, 5.0, 7.4, and 10.0. The results indicated that palonosetron hydrochloride is most stable at pH 5.0.

Example 2

Stabilizing Concentration Ranges

A formulation optimization study was performed using an experimental design software. Twenty-four lots of drug product were analyzed to investigate the appropriate concentration ranges for palonosetron hydrochloride (0.05 mg/mL to 5.0 mg/ml), citrate buffer (0 to 80 mM) and EDTA (0 to 0.10%). The level of EDTA and citrate buffer were selected based on the optimal formulation, which was shown to be formulated with EDTA 0.05% and 20 mM citrate buffer at pH 5.0. The results of this study indicated that palonosetron concentration was also a critical factor in chemical stability, with greatest stability seen at the lowest palonosetron concentrations.

Example 3

Tonicifying Agent

Formulations of palonosetron hydrochloride in citrate buffer were prepared including either a) sodium chloride or b) mannitol. The palonosetron hydrochloride formulation including mannitol showed superior stability. The optimum level of mannitol required for an isotonic solution was found to be 4.15%.

Example 4

Formulation I

The following is a representative, pharmaceutical formulation containing palonosetron that is useful for intravenous formulations, or other liquid formulations of the drug.

| Ingredient | mg/mL |
|---|---|
| Palonosetron Hydrochloride | 0.05* |
| Mannitol | 41.5 |
| EDTA | 0.5 |
| Trisodium citrate | 3.7 |
| Citric acid | 1.56 |
| WFI | q.s. to 1 ml |
| Sodium hydroxide solution and/or hydrochloric acid solution | pH 5.0 ± 0.5 |

*calculated as a free base

Example 5

Formulation II

The following is a representative pharmaceutical formulation containing palonosetron that is useful for oral formulations, or other liquid formulations of the drug.

| Ingredient | mg/mL |
|---|---|
| Palonosetron Hydrochloride | 0.05* |
| Mannitol | 150 |
| EDTA | 0.5 |
| Trisodium citrate | 3.7 |
| Citric acid | 1.56 |
| WFI | q.s. to 1 ml |
| Sodium hydroxide solution and/or hydrochloric acid solution | pH 5.0 ± 0.5 |
| Flavoring | q.s. |

*calculated as a free base

Example 6

Stability of Palonosetron without Dexamethasone

The physical and chemical stability of palonosetron HCl was studies in concentrations of 5 μg/mL and 30 μg/mL in 5% dextrose injection, 0.9% sodium chloride injection, 5% dextrose in 0.45% sodium chloride injection, and dextrose 5% in lactated Ringer's injection. The admixtures were evaluated over 14 days at 4° C. in the dark and for 48 hours at 23° C. under fluorescent light.

Test samples of palonosetron HCl were prepared in polyvinyl chloride (PVC) bags of the infusion solutions at concentrations of 5 and 30 μg/mL. Evaluations for physical and chemical stability were performed on samples taken initially and after 1, 3, 5, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC analytical technique.

All samples were physically stable throughout the study. The solution remained clear, and little or no change in particulate burden and haze level were found. Additionally, little or no loss of palonosetron HCl occurred in any of the samples at either temperature throughout the entire study period.

Example 7

Stability of Palonosetron with Dexamethasone

The physical and chemical stability of palonosetron HCl 0.25 mg admixed with dexamethasone (as sodium phosphate)

10 mg or 20 mg in 5% dextrose injection or 0.9% sodium chloride injection in polyvinyl chloride (PVC) minibags, and also admixed with dexamethasone (as sodium phosphate) 3.3 mg in 5% dextrose injection or 0.9% sodium chloride injection in polypropylene syringes at 4° C. in the dark for 14 days and at 23° C. exposed to normal laboratory fluorescent light over 48 hours, was studied.

Test samples of palonosetron HCl 5 μg/mL with dexamethasone (as sodium phosphate) 0.2 mg/mL and also 0.4 mg/mL were prepared in polyvinyl chloride (PVC) bags of each infusion solution. Additionally, palonosetron HCl 25 μg/mL with dexamethasone (as sodium phosphate) 0.33 mg/mL in each infusion solution were prepared as 10 mL of test solution in 20-mL polypropylene syringes. Evaluations for physical and chemical stability were performed on samples taken initially and after 1, 3, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC) analytical technique.

All samples were physically compatible throughout the study. The solutions remained clear, and little or no change in particulate burden and haze level were found. Additionally, little or no loss of palonosetron HCl and dexamethasone occurred in any of the samples at either temperature throughout the entire shay period.

This invention has been described with reference to its preferred embodiments. Variations and modifications of the invention will be obvious to those skilled in the art from the foregoing detailed description of the invention.

What is claimed is:

1. A pharmaceutically stable isotonic intravenous solution of palonosetron hydrochloride for reducing emesis or reducing the likelihood of emesis comprising
    a) from about 0.03 mg/mL to about 0.2 mg/mL palonosetron as palonosetron hydrochloride,
    b) a sterile pharmaceutically acceptable aqueous carrier comprising mannitol as a tonicity agent, at a pH of from 4.0 to 6.0, and
    c) EDTA in an amount of from 0.005 to 1.0 mg/mL.
2. The solution of claim 1 wherein the palonosetron is in a concentration of about 0.05 mg/mL as palonosetron hydrochloride.
3. The solution of claim 1 wherein the pH is from 4.5 to 5.5.
4. The solution of claim 1 wherein the pharmaceutically acceptable carrier further comprises citric acid.
5. The solution of claim 1 wherein:
    a) said palonosetron is present in a concentration of 0.05 mg/ml, as palonosetron hydrochloride; and
    b) said EDTA is present in a concentration of from 0.005 to 1.0 mg/ml.
6. The solution of claim 5 wherein said pH is from 4.5 to 5.5.

* * * * *

UNITED STATES PATENT AND TRADEMARK OFFICE
Certificate

Patent No. 7,960,424 B2            Patented: June 14, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Giorgio Calderari, Rancate (CH); Daniele Bonadeo, Varese (IT); Roberta Cannella, Varese (IT); Andrew Miksztal, Palo Alto, CA (US); Thomas Malefyt, Carmel Valley, CA (US); and Kathleen M. Lee, Palo Alto, CA (US)

Signed and Sealed this Fourteenth Day of May 2013.

*BRANDON J. FETTEROLF*
*Supervisory Patent Examiner*
Art Unit 1628
Technology Center 1600